United States Patent [19]
Matern et al.

[11] Patent Number: 6,160,205
[45] Date of Patent: Dec. 12, 2000

[54] CAFFEOYL-COA 3-O-METHYLTRANSFERASE GENES FROM PARSLEY

[75] Inventors: Ulrich Matern, Lahr; Rüdiger Hain, Langenfeld; Hans-Jörg Reif, Koeln; Klaus Stenzel, Duesseldorf; Jürgen E. Thomzik, Langenfeld, all of Germany

[73] Assignee: Bayer Aktiengesellschaft, Leverkusen, Germany

[21] Appl. No.: 08/988,054

[22] Filed: Dec. 10, 1997

Related U.S. Application Data

[62] Division of application No. 08/335,518, Nov. 7, 1994, Pat. No. 5,728,570, which is a continuation of application No. 07/874,466, Apr. 27, 1992, abandoned.

[30] Foreign Application Priority Data

May 30, 1991 [DE] Germany ............... 41 17 747

[51] Int. Cl.[7] .............. A01H 5/00; A01H 5/10; C12N 15/82
[52] U.S. Cl. ........................... 800/298; 435/419
[58] Field of Search ................. 536/23.2, 23.6; 435/320.1, 243, 419, 252.3, 468; 800/279, 301, 298

[56] References Cited

U.S. PATENT DOCUMENTS

| | | | |
|---|---|---|---|
| 4,652,639 | 3/1987 | Stobinsky | 435/91.52 |
| 5,728,570 | 3/1998 | Matern et al. | 435/252.3 |

OTHER PUBLICATIONS

Stam M, et al. "The silence of genes in transgenic plants." Ann. Bot. 79: 3–12, 1997.
Koziel MG, et al. "Optimizing expression of transgenes with an emphasis on post-transcriptional events." Plant Mol. Biol. 32: 393–405, 1996.
Smith CJS, et al. "Antisense RNA inhibition of polygalacturonase gene expression in transgenic tomatoes." Nature 334: 724–726, Aug. 25, 1988.
Plant Physiology, vol. 95, No. 1, Jan. 1991, pp. 137–143.
Plant Physiology, vol. 93, No. 1, May 1990, p. 15.
Journal of Biological Chemistry, vol. 266, No. 26, Sep. 1991, pp. 17416–17423.
Watson, James D., 1987, Molecular biology of the Gene, Menlo Park, CA, The Benjamin/Cummings Publishing Co., Inc., p. 313.
Katsube et. al., 1990, J. Biochem. 108: pp. 321–326.
Belrjavsky, et al. 1989, Nucleic Acids Research, 17(8):pp. 2919–2932.
Pakusch et al., Jan. 1991, Plant Physiol. 95: pp. 137–145.
Schmitt, et al. Sep. 1991, J. Biol. Chem. 266(26):pp. 17416–17423.
Bugos, et al. May 1990, Plant Physiol. 93 (1): 15.
J. Sambrook, et al., Molecular Cloning: A Laboratory Manual, Cold Spring Harbor Laboratory Press, 1989, pp. 9.47–9.51.
Z. Ye et al., The Plant Cell, 6: pp. 1427–1439 (1994);.
J. Zou et al., Plant Physiol. Biochem. 32: pp. 423–427 (1994).
J.T. Odell, et al., Nature 313: pp. 810–812 (1985).
J. Velten, et al. Embo Journal 3: pp. 2723–2730, (1984).
Jaye, M. et al. 1983, Nucleic Acids Research, 11(8): pp. 2325–2335.
Ullrich, A. et al. 1984, The EMBO Journal, 3 (2): pp. 361–364.
Lathe, R. 1985, The Journal of Molecular Biology, 183 (1): p. 1.
Fortkamp, E., et al. 1986, DNA, 5 (6): pp. 511–517.
Reimold, U. et al. 1983, The EMBO Journal, 2 (10): 1801–1805.
Wado, U., et al. 1991, Nucleic Acids Research, 19 (Supplement): 1981–1986, "Codon Usage tabulated from the Gene Bank genetic sequence data".
Fischer, et al. Current Opinion in Biotechnology, 1994, 5:125–130.
Pakusch, et al. "S–Adnosyl–L–methionine:trans–Caffeoyl–coenzyme $A_3$–O–Methyltransferase from Elicitor–Treated Parsley Cell Suspension Cultures", Archives of Biochemistry and Biophysics, vol. 271, No. 2, Jun. pp. 488–494, 1989.
Matern, et al., Aug. 1988, Bull. Liaison Groupe Polyphenols, 14: pp. 173–184.
Pakusch, et al. "Kinetic characterization of caffeoyl–coenzyme A–specific 3–O–Methyltransferase from elicitor–treated parsley cell suspensions", Plant Physiol. 96:327–330, 1991.
Dialog File 10 abstract, accession No. 92056130 of Barna et al. 1992, Physiological and molecular plant pathology 4094):247–257.

*Primary Examiner*—Amy Nelson
*Attorney, Agent, or Firm*—Norris, McLaughlin & Marcus, P.A.

[57] ABSTRACT

The present invention relates to new caffeoyl-CoA 3-O-methyltransferase genes isolated from parsley and their use for the transformation of vectors, host organisms and plants.

4 Claims, 1 Drawing Sheet

SEQUENCE LISTING (1) GENERAL INFORMATION:

(iii) NUMBER OF SEQUENCES: 1

(2) INFORMATION FOR SEQ ID NO: 1:

(i) SEQUENCE CHARACTERISTICS:
      (A) LENGTH: 1258 base pairs (B) TYPE: nucleic acid
(C) STRANDEDNESS: single stranded
(D) TOPOLOGY: linear (ii) MOLECULE TYPE: cDNA (vi) ORIGINAL SOURCE:
(A) ORGANISM: parsley
(H) CELL LINE: parsley cell culture;
Petroselinum crispum (ix) FEATURE:
(A) NAME/KEY: mature peptide
(B) LOCATION: 371 to 1093
(D) OTHER INFORMATION: codes for caffeoyl-CoA
3-O-methyltransferase
from parsley (ix) FEATURE:
(A) NAME/KEY: untranslated region
(B) LOCATION: 1 to 370; 1094 to 1258

(xi) SEQUENCE DESCRIPTION: SEQ ID NO:1:

```
CGAGCTCAGG CAGATGCACT TAATCAGCTA ACCACTGATG                    40

ACCTTGAAGG ACAGTTTGCA TTGCTGGAGA CTTCATCAGT                    80

CGATGATGAT CTTGCGAGTT TGAAGAAAGA ATTGTCTGGA                   120

AGTAGAAAGA AAGGACAGCT TCCGCCAGGA AGAACTACTG                   160

CTGCCTCAAA CTCGGGATTT CCATTCAGAG AAACTGAAAT                   200

TGAGAATGAG CTAAACGAAC TTAGGAGAAA AGCCGCTGAT                   240

TACTAAATAT ACAACTCTGC ATATGTTCAC TATGACTGCA                   280

CCTACTGCAT CTACAAATGT ACTTTTTGGT TGATTGTGGA                   320

CATTCTATAC ATACGTTAAG AGGCAGATTT GTCGTTTGGA                   360

CAAATTCCAG ATG GCT TCT AAT GGT GAA TCT AAA CAT TCA            400
            Met Ala Ser Asn Gly Glu Ser Lys His Ser
              1               5                  10

GAA GTT GGG CAC AAG AGT CTT TTG CAG AGT GAT GCT CTT           439
Glu Val Gly His Lys Ser Leu Leu Gln Ser Asp Ala Leu
                15                  20

TAT CAG TAT ATA CTT GAA ACA AGT GTG TAC CCA AGA GAA           478
Tyr Gln Tyr Ile Leu Glu Thr Ser Val Tyr Pro Arg Glu
     25                  30                  35

CCA GAG GCA ATG AAA GAG CTT AGA GAA GTC ACC GCA AAG           517
Pro Glu Ala Met Lys Glu Leu Arg Glu Val Thr Ala Lys
             40                  45

CAT CCA TGG AAT CTG ATG ACA ACA TCA GCT GAT GAA GGG           556
His Pro Trp Asn Leu Met Thr Thr Ser Ala Asp Glu Gly
50                  55                  60

CAG TTC TTG AAC ATG CTT TTG AAG CTC ATC AAT GCC AAA           595
Gln Phe Leu Asn Met Leu Leu Lys Leu Ile Asn Ala Lys
         65                  70                  75

AAC ACC ATG GAG ATT GGT GTT TAC ACT GGT TAT TCT CTC           634
Asn Thr Met Glu Ile Gly Val Tyr Thr Gly Tyr Ser Leu
                 80                  85

CTT GCC ACT GCC CTG GCT CTT CCA GAT GAT GGA AAG ATT           673
Leu Ala Thr Ala Leu Ala Leu Pro Asp Asp Gly Lys Ile
         90                  95                 100

TTG GCA ATG GAT ATC AAC AGA GAA AAC TAT GAA ATT GGA           712
Leu Ala Met Asp Ile Asn Arg Glu Asn Tyr Glu Ile Gly
                105                 110

TTA CCC ATC ATT GAA AAA GCT GGA GTT GGT CAC AAA ATT           751
```

-continued

```
Leu Pro Ile Ile Glu Lys Ala Gly Val Gly His Lys Ile
115                 120                 125
GAC TTC AGA GAA GGC CCA GCT TTG CCT GTT CTT GAT CAT                    790
Asp Phe Arg Glu Gly Pro Ala Leu Pro Val Leu Asp His
        130                 135                 140
ATG CTT GAA GAT GGA AAG TAT CAT GGA ACA TTT GAT TTT                    829
Met Leu Glu Asp Gly Lys Tyr His Gly Thr Phe Asp Phe
                145                 150
GTA TTT GTT GAT GCT GAC AAG GAT AAC TAT ATC AAC TAC                    868
Val Phe Val Asp Ala Asp Lys Asp Asn Tyr Ile Asn Tyr
        155                 160                 165
CAC AAG AGA TTA ATT GAT TTA GTA AAA ATC GGA GGA CTT                    907
His Lys Arg Leu Ile Asp Leu Val Lys Ile Gly Gly Leu
                170                 175
ATC GGC TAC GAC AAC ACC CTA TGG AAT GGT TCT GTG GCT                    946
Ile Gly Tyr Asp Asn Thr Leu Trp Asn Gly Ser Val Ala
180                 185                 190
CAG CCA GCT GAT GCT CCA ATG AGA AAG TAT GTA AGG TAC                    985
Gln Pro Ala Asp Ala Pro Met Arg Lys Tyr Val Arg Tyr
        195                 200                 205
TAC AGA GAC TTT GTG GAT TGA GCT TAA CAA GCT CTG GCC                   1024
Tyr Arg Asp Phe Val Ile Glu Leu Asn Lys Ala Leu Ala
                210                 215
GCT GAT CCC AGG ATT GAG ATC TGT ATG CTT CCT GTT GGT                   1063
Ala Asp Pro Arg Ile Glu Ile Cys Met Leu Pro Val Gly
        220                 225                 230
GAT GGA GTT ACC CTG TGC CGT CGT ATC AGC TGATTATCTA                    1103
Asp Gly Val Thr Leu Cys Arg Arg Ile Ser
                235                 240
ACTGAAATTT GAGATATTAT TTCACAATGT TTTAAGAAAT                           1143
GGAATACTTT TGCTTTGATT GTATCTTCCT ATGTTTCTTG                           1183
TTGAATTTGC AATGTGCATT ATTGATGATG AATATATTCA                           1223
TAATTGATGT TGAAAAAAAA AAAAAAAAAA AAAAA                                1258
```

CAFFEOYL-COA 3-O-METHYLTRANSFERASE GENES FROM PARSLEY

This is a divisional of application Ser. No. 08/335,518, filed Nov. 7, 1994, issued as U.S. Pat. No. 5,728,570, which is a continuation of Ser. No. 07/874,466, filed on Apr. 27, 1992, now abandoned.

BACKGROUND OF THE INVENTION

1. Field of the Invention

The present invention relates to new caffeoyl-CoA 3-O-methyltransferase genes (called CCoAMT genes below) isolated from plants and to their use for the transformation of vectors, host organisms and plants and for the generation of plants which have an increased resistance to pests.

2. Description of the Related Art

The enzyme caffeoyl-CoA 3-O-methyltransferase, called CCoAMT below, catalyses the methylation of caffeoyl-CoA in a biosynthesis route, which has only recently been described, which leads from trans-4-coumaroyl-CoA to trans-feruloyl-CoA (Matern, U., and Kneusel, R. E. 1988, Phytoparasitica 16:153–170; Kneusel, R. E., Matern, U., and Nicolay, K. 1989, Arch. Biochem. Biophys. 269:455 to 462; and Pakusch, A. -E., Kneusel, R. E., and Matern, U., 1989, Arch. Biochem. Biophys. 271:488 to 494).

Under fungal attack, plants reinforce their cell wall very rapidly by incorporation of cinnamic acids, followed by cross-linking thereof to give polymeric structures or build-up of lignin. Under these conditions, feruloyl-CoA is the preferred acyl donor both for the esterification of cell wall polysaccharides and for lignification (reduction to coniferyl alcohol). The speed and extent of the change in the cell wall essentially determine the course of the infection and the fate of the plants, "hypersensitive reaction" characterising complete resistance of the plants, associated with a particularly severe and rapid change in the cell wall and the death of the cells directly affected. This hypersensitive reaction is also observed in the resistance reaction of plants to virus infections. It has only recently been discovered that feruloyl-CoA is not formed in vivo in all cases by activation of ferulic acid, but is also formed by reaction of coumaroyl-CoA. The caffeoyl-CoA-specific methyl-transferase which participates in this reaction has scarcely any homology with previously known enzymes (Pakusch, A. -E., Matern, U., and Schiltz, E., 1991, Plant Physiol. 95:137 to 143), is taxonomically widespread in plants and can be induced therein by, for example, fungal attack.

A large proportion of the world harvest of crop plants is constantly destroyed by pests (in 1967 the loss of potential harvest was 35%; compare Chemistry of Pesticides, published by K. H. Buchel, John Wiley & Sons, New York, 1983, page 6). There is therefore an urgent need to research and utilise all possibilities which are capable of reducing or preventing attack of crop plants by pests.

SUMMARY OF THE INVENTION

The new caffeoyl-CoA 3-O-methyltransferase genes, called CCoAMT genes below, have now been found, which can be incorporated into the hereditary factors (the genome) of plants which generate no CCoAMT or only inadequate CCoAMT, whereby an increased resistance of these plants to pests can be brought about.

It is surprising that it has been possible to find a new type of resistance genes which can be incorporated as foreign or additional DNA into the genome of plants, whereby an increased resistance of the resulting transgenic plants to pests is achieved. A particular advantage of the present invention is that—in contrast to, for example, the case of increased accumulation of phytoalexins—it is not aimed at the generation of potentially toxic metabolites. There are therefore also no toxicological reservations, because the aim is the rapid synthesis in the transformed plants of predominantly insoluble, antibiotically inactive compounds which should function as physical barriers or prevent possible pathogen-induced, enzymatic lysis of cell wall polysaccharides by acylation of the "substrate". In contrast to the transformation of plants with genes of lytic enzymes, such as, for example, lysozyme or also chitinase, which at best can become selectively active, the increased readiness of plants to reinforce the cell wall offers protection against every form of pathogens, including viruses. The present invention here therefore follows a novel principle of plant protection with wide application.

BRIEF DESCRIPTION OF THE DRAWINGS

The invention will now be described in more detail with reference to the drawings, wherein.

DETAILED DESCRIPTION OF THE INVENTION

Figure 1:
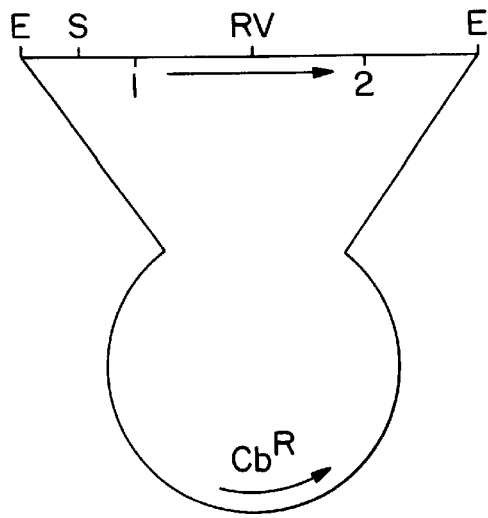
FIG. 1 represents a diagram of the plasmid pL2-4 which contains the protein-encoding sequence of the CCoAMT gene (compare also SEQ ID NO: 1) on the EcorI fragment

By CCoAMT genes, there are to be understood any nucleic acid (DNA) which, after its transcription into RNA and translation into protein, causes the formation of an enzyme which has the properties of a CCoAMT, this nucleic acid being isolated from its natural environment or integrated into a vector or contained as "foreign" DNA or as "additional" DNA in a prokaryotic or eukaryotic DNA. By CCoAMT genes there are also to be understood those CCoAMT genes which contain, at their start and/or end, additional DNA sequences which do not or do not substantially impede the function of the genes. These DNA sequences, which are also called "gene units", are formed, for example, by excision with restriction enzymes, since no cleavage sites are available for customary restriction enzymes exactly at the start and at the end of the gene. The CCoAMT genes or the gene units can also carry at their ends DNA sequences which are appropriate for their handling (for example "linkers").

The CCoAMT genes (or the gene units) can exist in the form in which they are contained in the genome of plants ("genomic" form, including sequences which do not encode CCoAMT and/or do not have a regulatory action (such as introns)), or in a form which corresponds to the cDNA ("copy" DNA) which is obtainable via mRNA with the aid of reverse transcriptase/polymerase (and no longer contains introns). The CCoAMT genes can also be present in partially or completely synthetic form. By synthetic genes there are also understood those which are formed by newly joining of parts of natural genes.

DNA segments or DNAs in the CCoAMT genes (or the gene units) according to the invention can be replaced by other DNA segments or DNAs which have essentially the same action.

In the present connection, by "foreign" DNA there is to be understood DNA (in particular genes or gene units or componenents thereof) which does not occur naturally in a certain prokaryotic or eukaryotic genome, but is taken up in this genome only as a result of intervention by man. "Additional" DNA (in particular genes or gene units or components thereof) is intended to mean DNA which, although it occurs naturally in the particular prokaryotic or eukaryotic genome, has been taken up in this genome in an additional amount as a result of intervention by man. One or more copies of the "foreign" DNA or "additional" DNA can be incorporated, depending on requirements and on the nature of the case in question.

CCoAMT which is formed in plants or plant cells with the assistance of the CCoAMT genes (or the gene units) according to the invention means any enzyme which acts like CCoAMT and, in plants, increases their resistance to pests.

The preferred CCoAMT genes according to the invention are characterised in that they hybridise with the CCoAMT-cDNA sequence contained in the plasmid pL2-4 or its components or with the cDNA sequence according to SEQ ID No: 1 or its components and encode CCoAMT.

CCoAMT genes which are preferred according to the invention are the CCoAMT genes which occur in parsley (*Petroselinum crispum*), carrots (*Daucus carota*), carnation (*Dianthus caryophyllus*) and safflower (*Carthamus tinctorius*), particularly preferably in parsley, and can be isolated from these.

The CCoAMT gene which is present (as a gene unit) in the form of the cDNA on the plasmid pL2-4 (which is described below in more detail) and the DNA sequences which have essentially the same action are especially preferred as the CCoAMT gene according to the invention.

The cDNA contained on the plasmid was isolated from parsley. It consists of a 5' untranslated leader sequence 370 nucleotides long and the complete protein-encoding region from position 371 to position 1093, followed by 67 nucleotides of a 3' untranslated sequence. The entire fragment was provided with EcoRI linkers on both sides and cloned into the vector pGEM 7 (Promega Corp. Madison, Wis., USA). The residual sequence of the 3' untranslated region from position 1160 to 1258 is not present on the plasmid pL2-4. This poly-adenylation sequence can be prepared synthetically or replaced by another poly-A sequence. The complete cDNA sequence can be seen from sequence protocol SEQ ID No: 1.

The 5' untranslated region, the complete encoding region and 67 nucleotides of the 3' untranslated region can be isolated in the customary manner with EcoRI on a fragment about 1170 long.

The chimaeric gene fusions of the TR promoter or the 35 S promoter with the protein-encoding region of the CCoAMT genes, preferably of the gene from parsley, inparticular of the gene which corresponds to the cDNA on the plasmid pL2-4, may be mentioned as particularly preferred. It has been found that the CCoAMT genes which occur in plants have wide regions of DNA sequence homology. On the basis of the sequence homology, the CCoAMT genes according to the invention can therefore be isolated from plants in a simple manner with the aid of the cDNA contained on the plasmid pL2-4 or its components or the sequence information according to SEQ ID No: 1 in the customary manner using the known methods of molecular biology.

Possible plants from which CCoAMT genes according to the invention can be isolated are practically all the monocotyledonous or dicotyledonous plants, preferably dicotyledonous plants, parsley, carrot, safflower and carnation being mentioned by way of example and as preferred.

As already mentioned, the CCoAMT gene, or the encoding region thereof, which corresponds to the cDNA which lies on the plasmid pL2-4 is preferred according to the invention. The gene or the coding region of the gene can be obtained in the customary manner with the aid of the cDNA.

The *Escherichia coli* strain DS pL2-4 contains the plasmid pL2-4. This strain has been deposited at the Deutsche Sammlung von Mikroorganismen (DSM) [German Collection of Microorganisms], Mascheroder Weg 1b, D-3300 Braunschweig, Federal Republic of Germany, in accordance with the conditions of the Budapest Treaty on the International Recognition of Deposition of Microorganisms for the Purposes of Patent Proceedings (deposition date: May 28, 1991). It has been given deposition number DSM 6536.

The present invention also relates to this strain and its mutants. The plasmid pL2-4 deposited in this host can easily be obtained in the required amounts in the customary manner by multiplication of the strain and subsequent isolation of the plasmid.

Functionally complete genes, such as the CCoAMT genes according to the invention, consist of a component which has a regulatory action (in particular a promoter) and the structural gene which codes for the protein CCoAMT.

Both parts of the gene can be used independently of one another. It is thus possible to fuse the component having the regulatory action with another DNA sequence (deviating from the CCoAMT gene) which is to be expressed after incorporation into the plant genome. Since only a few isolated promoters which can display their action in plants or plant cells are known, the promoters of the CCoAMT genes, to which the present invention likewise relates, are useful aids in the generation of transformed plants or plant cells.

It is also possible to have the CCoAMT structural genes preceded by a "foreign" component having a regulatory action. This could be advantageous if only specific regulatory active gene components (for example those endogenous to the plant) can have a sufficient action in certain plants. The CCoAMT structural genes are therefore valuable units which can be used independently and, as already mentioned, the present invention also relates to them. The CCoAMT genes according to the invention can be separated into the components having a regulatory action and the structural genes by the customary methods. It is also possible to combine components of different naturally occurring CCoAMT genes to give new functional "synthecic" genes. The complete naturally occurring CCoAMT genes (or the gene units) according to the invention are preferably used. The CCoAMT structural gene which corresponds to the cDNA contained in the plasmid pL2-4 is preferred according to the invention.

It is possible, with the aid of customary methods, to incorporate the CCoAMT genes (or the gene units) or their components in one or several copies (for example in tandem arrangement), preferably once, into any desired prokaryotic (preferably bacterial) or eukaryotic (preferably plant) DNA as "foreign" or "additional" DNA. Thus, for example, the protein-encoding DNA corresponding to the cDNA can be provided with regulatory sequences and incorporated into plants. The present invention relates to the recombinant DNA "modified" in this way, which can be used, for example, for the transformation of plants or plant cells and is contained in the plants or plant cells after the transformation.

The CCoAMT genes (or the gene units) and/or their components and the recombinant DNA can be contained as "foreign" or "additional" DNA in vectors (in particular plasmids, cosmids or phages), in transformed microorganisms (preferably bacteria, in particular Gram-negative bacteria, such as E. coli) and in transformed plant cells and plants or in the DNA thereof. The present invention relates to such vectors, transformed microorganisms (which can also contain these vectors) and the transformed plant cells and plants and DNA thereof.

As already indicated, according to the invention the CCoAMT genes (or the gene units) are incorporated in one or several copies (at the same or different points of the genome) into the natural plant genome, it also being possible for different CCoAMT genes to be combined with one another. In the case of plants which already have the capacity for CCoAMT synthesis, the incorporation of one or more CCoAMT genes according to the invention can lead to considerably improved resistance properties. In the case of plants which contain no CCoAMT genes, an increased resistance to pests is likewise achieved by incorporation of such genes. If appropriate, only the structural genes according to the invention are used, these being preceded by a regulatory DNA element which may have been isolated from the particular plant.

The increased resistance of the transformed plant cells and plants according to the invention is of importance for agriculture and forestry and for cultivation of ornamental plants, cultivation of medicinal plants and plant breeding. It is also advantageous in the culture of plant cells, for example for the production of pharmaceutically usable substances, to have available plant cells which have increased resistances to attack by microbial pests, in particular fungi.

The present invention thus also relates to a process for the preparation of transformed plant cells (including protoplasts) and plants (including plant parts and seeds) having an increased resistance to pests, which is characterised in that (a) one or more CCoAMT genes (or gene units) and/or components of the CCoAMT genes (or of the gene units) and/or recombinant DNA according to the invention are inserted into the genome of plant cells (including protoplasts), and if appropriate (b) complete transformed plants are regenerated from the transformed plant cells (including protoplasts) and if appropriate propagated, and if appropriate (c) the desired plant parts (including seeds) are obtained from the resulting transformed plants of the parent generation or further generations obtained therefrom.

Process steps (a), (b) and (c) can be carried out in the customary manner by known processes and methods.

The present invention also relates to transformed plant cells (including protoplasts) and plants (including plant parts and seeds) which contain one or more CCoAMT genes (or gene units) and/or components of the CCoAMT genes (or of the gene units) as "foreign" or "additional" DNA, and to those transformed plant cells and plants which are obtainable by the above processes.

The present invention also relates to the:

(a) use of the CCoAMT genes (or of the gene units) and/or their components and/or the recombinant DNA according to the invention and/or the recombinant vectors according to the invention and/or the transformed microorganisms according to the invention for the transformation of plant cells (including protoplasts) and plants (including plant parts and seeds), the (b) use of the transformed plant cells (including protoplasts) and plants (including plant parts and seeds) according to the invention for the generation of propagation material and for the generation of new plants and propagation material thereof, the (c) use of the CCoAMT genes according to the invention (or of the gene units) and/or their components and/or the recombinant DNA according to the invention for combating pests and the d) use of the cDNA contained on the plasmid pL2-4 or its components and of the DNA sequences corresponding to the sequence information according to sequence protocol SEQ ID NO:1 for isolation of CCoAMT genes or components thereof from plants and for the determination of CCoAMT genes in plants.

There are a number of different methods available for inserting the CCoAMT genes or the gene units or their components into the genetic material of plants or plant cells as "foreign" or "additional" DNA. The gene transfer can be carried out by the generally customary known methods, the expert being able to determine without difficulty the particular method suitable.

The Ti plasmid from Agrobacterium tumefaciens is available as a particularly favourable and widely applicable vector for the transfer of foreign DNA into genomes of dicotyledonous and monocotyledonous plants. The genetic material which encodes CCoAMT is inserted into the T-DNA of suitable Ti plasmids together with regulatory DNA sequences (for example Zambryski et al. 1983) and transferred by infection of the plants, infection of plant parts or plant tissues, such as, for example, of leaf discs, stems, hypocotyls, cotyledons, meristems and tissues issuing therefrom, such as, for example, secondary embryos and calli, or by coculture of protoplasts with *Agrobacterium tumefaciens*.

An alternative is the incubation of purified DNA which contains the desired gene in plant protoplasts (for example Hain et al., 1985; Krens et al., 1982; Paszkowski et al., 1984) in the presence of polycations or calcium salts and polyethylene glycol.

The DNA uptake can also additionally be promoted by an electric field (electroporation) (for example Fromm et al., 1986).

The DNA can also be introduced in a known manner via plant pollen, by "shooting" the pollen with physically accelerated particles which carry the DNA (compare EP-A 0,270, 356).

The plants are regenerated in a known manner with the aid of suitable nutrient media (for example Nagy and Maliga 1976).

In a preferred embodiment of the process according to the invention, the cDNA from the plasmid pL2-4 is cloned into an expression vector (for example pRT101, Töpfer et. al. 1988). The chimaeric constructed gene is then isolated with the restriction enzyme Hind III and transferred in an intermediate vector (for example pCV001, Koncz and Schell 1986) to *Agrobakterium tumefaciens* (Koncz and Schell 1986).

Alternatively, the chimaeric constructed gene is cloned into the Hind III position of the plasmid PlGVneo 1103 (Hain et. al. 1985), and in a particularly preferred embodiment the chimaeric constructed gene in the plasmid pLGVneo 1103 is transferred in the customary manner to plant protoplasts by direct gene transfer (for example Hain et. al. 1985). The plasmid can be in circular form, but is preferably in linear form here.

If this plasmid is used with a reporter gene, the kanamycin-resistant protoplasts are then checked for expression of CCoAMT.

Transformed (transgenic) plants or plant cells are generated by the known methods, for example by leaf disc transformation (for example Horsch et al. 1985) by coculture of regenerating plant protoplasts or cell cultures with Agrobacterium tumefaciens (for example Marton et al. 1979, Hain et al. 1985) or by direct DNA transfection. Resulting transformed plants are detected either by selection for expression of the reporter gene, for example by phosphorylation of kanamycin sulphate in vitro (Reiss et al. 1984; Schreier et al. 1985) or by the expression of nopaline synthase (according to Aerts et al. 1983) or CCoAMT by Northern blot analysis and Western blot analysis. The CCoAMT can also be detected in a known manner with the aid of specific antibodies in transformed plants.

Culture of the transformed plant cells and regeneration to give complete plants are carried out by the generally customary methods with the aid of the particular suitable nutrient media.

Both the transformed plant cells and the transformed plants which contain the CCoAMT genes according to the invention (or the gene units) and to which the present invention relates exhibit a considerably higher resistance to pests, in particular phytopathogenic fungi.

In connection with the present invention, the term "plants" denotes both complete plants and also parts of plants, such as leaves, seeds, tubers, cuttings and the like. "Plant cells" include protoplasts, cell lines, plant calli and the like. "Propagation material" denotes plants and plant cells which can be used for propagation of the transformed plants and plant cells, and the present invention thus also relates to this material.

In the present connection, the term "DNA sequences having essentially the same action" means that the invention also relates to those modifications in which the function of the CCoAMT genes and their components is not impaired such that CCoAMT is no longer formed or the regulatory gene component is no longer active. Corresponding modifications can be made by replacement, addition and/or removal of DNA sections, individual codons and/or individual nucleotides.

In the case of microorganisms which can be used according to the invention, "mutants" denotes those modified microorganisms which still have the features essential for implementation of the invention, and in particular contain the particular plasmids.

The plants which can be given resistance or an increased resistance to pests by incorporation (transformation) of the CCoAMT genes according to the invention (or the gene units) include practically all plants. There is of course a particular need for generating resistance in crop plants, such as forest plants, for example spruce, fir, Douglas fir, pine, larch, beech and oak, as well as plants which supply foodstuffs and raw materials, for example cereals (in particular wheat, rye, barley, oats, millet, rice and maize), potatoes, leguminous plants (such as pulses and in particular alfalfa and soybeans), vegetables (in particular cabbage varieties and tomatoes), fruit (in particular apples, pears, cherries, grapes, citrus fruits, pineapples and bananas), oil palms, tea, cacao and coffee shrubs, tobacco, sisal and cotton, and in medicinal plants, such as Rauwolfia and Digitalis. Potatoes, tomatoes and leguminous plants may be mentioned particularly preferably. The CCoAMT genes according to the invention are preferably incorporated into the genome of plants as "foreign" DNA.

As pests against which resistances or increased resistances can be achieved with the aid of the CCoAMT genes according to the invention there may be mentioned animal pests, such as insects, mites and nematodes, as well as microbial pests, such as phytopathogenic fungi, bacteria and viruses. Microbial pests, in particular phytopathogenic fungi, are particularly singled out.

The harmful insects include, in particular, insects of the orders:

Orthoptera, Dermaptera, Isoptera, Thysanoptera, Heteroptera, Homoptera, Lepidoptera, Coleoptera, Hymenoptera and Diptera.

The harmful mites include, in particular: Tarsonemus spp., Panonychus spp. and Tetranychus spp.

The harmful nematodes include, in particular: Pratylenchus spp., Heterodera spp. and Meloidogyne spp.

The microbial pests include, in particular, the phytopathogenic fungi:

Plasmodiophoromycetes, Oomycetes, Chytridiomycetes, Zygomycetes, Ascomycetes, Basidiomycetes and Deuteromycetes.

The phytopathogenic bacteria include, in particular, the Pseudomonadaceae, Rhizobiaceae, Enterobacteriaceae, Corynebacteriaceae and Streptomycetaceae.

The virus diseases include, in particular, mosaic, dwarfing and yellowing viroses.

Some causative organisms of viral, fungal and bacterial diseases which come under the generic names listed above may be mentioned as examples, but not by way of limitation: barley yellow dwarf virus (BYDV), potato virus Y (PVY), cucumber mosaic virus (CMV), watermelon mosaic virus (WMV), Tristeza virus, tobacco mosaic virus (TMV), tobacco necrosis virus (TNV), beet necrotic yellow vein virus (BNYVV), rhizomania virus.

Xanthomonas species, such as, for example, *Xanthomonas campestris* pv. *oryzae;*

Pseudomonas species, such as, for example, *Pseudomonas syringae* pv. *lachrymans;*

Erwinia species, such as, for example, *Erwinia amylovora;*

Pythium species, such as, for example, *Pythium ultimum;*

Phytophthora species, such as, for example, *Phytophthora infestans;*

Pseudoperonospora species, such as, for example, *Pseudoperonospora humuli* or *Pseudoperonospora cubense;*

Plasmopara species, such as, for example, *Plasmopara viticola;*

Peronospora species, such as, for example, *Peronospora pisi* or *P. brassicae;*

Erysiphe species, such as, for example, *Erysiphe graminis;*

Sphaerotheca species, such as, for example, *Sphaerotheca fuliginea;*

Podosphaera species, such as, for example, *Podosphaera leucotricha;*

Venturia species, such as, for example, *Venturia inaequalis;*

Pyrenophora species, such as, for example, *Pyrenophora teres* or *P. graminea*

(conidia form: Drechslera, syn: Helminthosporium);

Cochliobolus species, such as, for example, *Cochliobolus sativus*

(conidia form: Drechslera, syn: Helminthosporium);

Uromyces species, such as, for example, *Uromyces appendiculatus;*

Puccinia species, such as, for example, *Puccinia recondita;*

Tilletia species, such as, for example, *Tilletia caries;*

Ustilago species, such as, for example, *Ustilago nuda* or *Ustilago avenae;*

Pellicularia species, such as, for example, *Pellicularia sasakii*;

Pyricularia species, such as, for example, *Pyricularia oryzae*;

Fusarium species, such as, for example, *Fusarium culmorum*;

Botrytis species, such as, for example, *Botrytis cinerea*;

Septoria species, such as, for example, *Septoria nodorum*;

Leptosphaeria species, such as, for example, *Leptosphaeria nodorum*;

Cercospora species, such as, for example, *Cercospora canescens*;

Alternaria species, such as, for example, *Alternaria brassicae*; and

Pseudocercosporella species, such as, for example, *Pseudocerco sporella herpotrichoides*. Helminthosporium carbonum may furthermore be mentioned.

The present invention shall be illustrated in more detail with the aid of the following embodiment examples:

1. Isolation of the gene for CCoAMT from parsley

Plants and cell cultures from parsley (*Petroselinum crispum*) contain the genes for CCoAMT which cause the formation of CCoAMT (size of the protein 27,000 D; reaction with specific antiserum).

The known processes and methods of molecular biology such as are described in detail, for example, in the following handbook were used in the isolation of the CCoAMT genes: Maniatis, T., Fritsch, E. F., Sambrook, J.: Molecular Cloning: A Laboratory Manual; Cold Spring Harbor Laboratory, Second Edition 1989.

A "gene library" for parsley is first established: genomic DNA from enriched cell nuclei (Bedbrook, J., Plant Molecular Biology Newsletter 2, 24, 1981) is cut with the restriction enzyme NdeII such that DNA fragments having an average length of about 12,000 nucleotide pairs are formed. These fragments are cloned into the BamHI site of the lambda phage EMBL4 (Frischauf et al., J. Mol. Biol. 170, 827–842, 1983), and the phages are multiplied in *E. coli*. The phage population in its entirety contains, cloned in sub fragments, the total genomic DNA of parsley, and therefore also the genes for CCoMAT.

The genes for CCoMAT, their mRNA and the CCoMAT synthase cDNA each contain the same nucleic acid sequences, since they can be derived from one another (gene→mRNA→cDNA). This means that the genes for CCoMAT can be identified by specific hybridisation with CCoMAT-cDNA (compare SEQ ID NO:1) or with specific oligonucleotides which can be derived from this sequence. The phages with the genes are identified by hybridisation, and then isolated and multiplied. The genomic DNA from parsley cloned in this phage is mapped further by analysis with various restriction enzymes, and the position of the CCoMAT genes is determined by further hybridisation experiments with cDNA sequences or synthetic oligonucleotides. Finally, the gene units are cut out of the phage by digestion with restriction enzymes, cloned in the correspondingly cut plasmid vector and multiplied as recombinant plasmids.

Because of the sequence homologies, DNA sequences which correspond to the sequences contained in the cDNA on the plasmid pL2-4 can be used as probes for isolation of other CCoAMT genes according to the invention.

2. Transformation of tobacco a) Culture of tobacco shoots and isolation of tobacco protoplasts:

*Nicotiana tabacum* (Petit Havanna SR1) is propagated as a sterile shoot culture on hormone-free LS medium (Linsmaier and Skoog 1965). Shoot sections are transferred to fresh LS medium at intervals of about 6–8 weeks. The shoot cultures are kept in 12 hours of light (1000–3000 lux) in a culture room at 24–26° C.

For the isolation of leaf protoplasts, about 2 g of leaves (about 3–5 cm long) are cut into small pieces (0.5 cm×1 cm) with a fresh razor blade. The leaf material is incubated in 20 ml of enzyme solution consisting of K3 medium (Nagy and Maliga 1976), 0.4 M sucrose, pH 5.6, 2% of Zellulase R10 (Serva) and 0.5% of Macerozym R10 (Serva) at room temperature for 14–16 hours. The protoplasts are then separated from cell residues by filtration over a 0.30 mm and 0.1 mm steel sieve. The filtrate is centrifuged at 100× g for 10 minutes. During this centrifugation, intact protoplasts float and collect in a band at the top margin of the enzyme solution. The pellet of cell residues and the enzyme solution are sucked off with a glass capillary. The prepurified protoplasts are made up to 10 ml with fresh K3 medium (0.4 M sucrose as an osmotic agent) and floated again. The washing medium is sucked off and the protoplasts are diluted to $1-2\times10^5$/ml for culture or subsequent infection with Agrobacteria (coculture). The protoplast concentration is determined in a counting chamber.

b) Construction of a chimaeric CCoAMT gene and transfer into *Agrobacterium tumefaciens*

The EcoRI fragment from pL2-4 (about 1.2 kb) is cloned into the EcoRI position of the vector pRT 101 (Töpfer et. al. 1988). This gives the cDNA the 35 S promoter of CaMV on its 5' end and a polyadenylation sequence from CaMV on its 3' end. This chimaeric constructed gene can then be isolated functionally as a fragment of about 1.9 kb by cleavage with HindIII. This HindIII fragment can then be transferred into an intermediate vector, for example pCV001 (Koncz and Schell, 1986) by the customary methods. Instead of the vectors mentioned, any other desired expression vectors and intermediate vectors which have corresponding cleavage sites can be employed, the expert easily being able to make a suitable choice on the basis of the above information. The resulting intermediate vector, which contains the CCoAMT gene, is transferred to *Agrobacterium tumefaciens* which contains a functional vir region (Koncz and Schell 1986, van Haute et.al. 1983).

c) Transformation of regenerating tobacco protoplasts by coculture with *Agrobacterium tumefaciens*:

The method of Marton et al. 1979 is used below, with minor modifications. The protoplasts are isolated as described and incubated in a density of $1-2\times10^5$/ml in K3 medium (0.4 M sucrose, 0.1 mg/l of NAA, 0.2 ml in K3 medium (0.4 M sucrose, 0.1 mg/l of NAA, 0.2 mg of kinetin) for 2 days in the dark and one to two days under weak light (500 lux) at 26° C. As soon as the first divisions of the protoplasts occur, 30 μl of an Agrobacterium suspension according to b) in minimal A (Am) medium (density about $10^9$ Agrobacteria/ml) are added to 3 ml of regenerating protoplasts. The duration of the coculture is 3–4 days at 20° C. in the dark. The tobacco cells are then introduced into 12 ml centrifuge tubes, diluted to 10 ml with seawater (600 mOsm/kg) and pelleted at 60× g for 10 minutes. This washing operation is repeated a further 1–2 times in order to remove the majority of the Agrobacteria. The cell suspension is cultured in a density of $5\times10^4$/ml in K3 medium (0.3 M sucrose) with 1 mg/l of NAA (naphthyl-1-acetic acid), 0.2 mg/l of kinetin and 500 mg/l of the cephalosporin antibiotic cefotaxime. The cell suspension is diluted with fresh K3 medium every week and the osmotic value of the medium is reduced gradually by 0.05 M sucrose (about 60 mOsm/kg) per week. Selection with kanamycin (100 mg/l of kanamycin sulphate (Sigma), 660 mg/g of active km) is started 2–3 weeks after the coculture in an agarose "bead type culture" (Shillito et al. 1983). Kanamycin-resistant colonies can be distinguished from the background of retarded colonies 3–4 weeks after the start of the selection.

d) Direct transformation of tobacco protoplasts with DNA. Calcium nitrate-PEG transformation.

Figure 2:
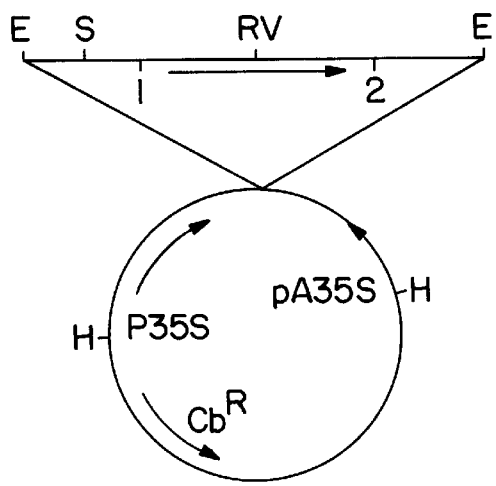
FIG. 2 represents a diagram of the plasmid pCV001:CCoAMT which contains a chimaeric CCoAMT gene.
Figure 3:
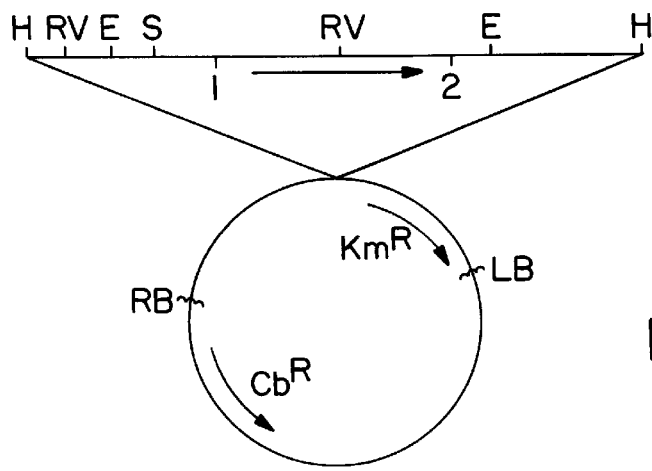
FIG. 3 represents a diagram of the plasmid pCV001:CCoAMT which contains a chimaeric CCoAMT gene.

About $10^6$ protoplasts in 180 µl of K3 medium are carefully mixed in a Petri dish with 20 µl of aqueous DNA solution which contains 20 µg of plasmid pCV001::CCoAMT (compare FIG. 3). The plasmid pCV001::CCoAMT is obtainable by known methods from the plasmid pCV001, pRT101 and pL2-4 (compare FIGS. 1–3). 200 µl of fusion solution (0.1 M calcium nitrate, 0.45 M mannitol, 25% of polyethylene glycol (PEG 6000), pH 9) are then carefully added. After 15 minutes, 5 ml of washing solution (0.275 M calcium nitrate pH 6) are added, and after a further 5 minutes the protoplasts are transferred into a centrifuge tube and pelleted at 60× g. The pellet is taken up in a small amount of K3 medium and cultured as described in the next section. Alternatively, the protoplasts can be transformed as described by Hain et al. 1985.

e) Culture of the protoplasts incubated with DNA and selection of kanamycin-resistant calli:

A modified "bead type culture" technique (Shillito et al. 1983) is used for the culture and selection of kanamycin-resistant colonies described below. One week after treatment of the protoplasts with DNA (compare d), 3 ml of the cell suspension are mixed with 3 ml of K3 medium (0.3 M sucrose+hormones; 1.2% (Seaplaque) of LMT agarose (low melting agarose, Marine Colloids) in 5 cm Petri dishes. For this purpose, the agarose is autoclaved in the dry state and, after addition of K3 medium, is boiled up briefly in a microwave oven. After the agarose has solidified, the agarose discs ("beads") are transferred into 10 cm Petri dishes with the embedded tobacco microcalli for further culture and selection, and in each case 10 ml of K3 medium (0.3 M sucrose, 1 mg/l of NAA, 0.2 mg/l of kinetin) and 100 mg/l of kanamycin sulphate (Sigma) are added. The liquid medium is changed every week. During this procedure, the osmotic value of the medium is reduced in stages.

The replacement medium (K3+km) is reduced by 0.05 M of sucrose (about 60 mOsm) per week.

Timetable of the selection of kanamycin-resistant tobacco colonies after DNA transformation:

| 0.4 M | 0.3 M | 0.25 M | 0.20 M | 0.15 M | 0.10 M | sucrose in the liquid medium |
|-------|-------|--------|--------|--------|--------|------------------------------|
| A E S |       |        |        | K      |        |                              |
| 1     | 2     | 3      | 4      | 5      | 6      | weeks after DNA Uptake       |
| (K3 medium 1 mg of NAA, 0.2 mg of kinetin) |

A = DNA uptake
E = embedding in agarose
S = selection with kanamycin (100 mg/l of kanamycin sulphate)
K = kanamycin-resistant colonies can be clearly distinguished from the background f) Regeneration of kanamycin-resistant plants:

As soon as the kanamycin-resistant colonies have reached a diameter of about 0.5 cm, half of them are placed on regeneration medium (LS medium, 2% of sucrose, 0.5 mg/l of benzylaminopurine BAP) and kept in the culture room in 12 hours of light (3000–5000 lux) at 24° C. The other half are propagated as a callus culture on LS medium with 1 mg/l of NAA, 0.2 mg/l of kinetin, 0.1 mg/l of BAP and 100 mg/l of kanamycin sulphate. When the regenerated shoots are about 1 cm in size, they are cut off and placed on ½ LS medium (1% of sucrose, 0.8% of agar), without growth regulators, for rooting. The shoots are rooted on ½ MS medium with 100 mg/l of kanamycin sulphate and later transferred into soil.

g) Transformation of leaf discs by *Agrobacterium tumefaciens*

For transformation of leaf discs (Horsch et al. 1985), leaves about 2–3 cm long from sterile shoot cultures are stamped into discs of 1 cm diameter and incubated with a suspension of appropriate Agrobacteria (about $10^9$/ml) (compare c) in Am medium, see below) for about 5 minutes. The infected pieces of leaf are kept on MS medium (see below) without hormones for 3–4 days at about 24° C. During this period, Agrobacterium grows over the pieces of leaf. The pieces of leaf are then washed in MS medium (0.5 mg/ml of BAP, 0.1 mg/ml of NAA) and placed on the same medium (0.8% of agar) with 500 µg/ml of cefotaxime and 100 µg/ml of kanamycin sulphate. The medium should be renewed after two weeks. Transformed kanamycin-resistant shoots are visible after a further 2–3 weeks.

Biochemical detection method of transformation

Neomycin phosphotransferase (NPT II) enzyme test:

NPT II activity in plant tissue is detected as follows by in situ phosphorylation of kanamycin as described by ReiB et al. (1984) and modified by Schreier et al. (1985). 50 mg of plant tissue are homogenised on ice in 50 µl of extraction buffer (10% of glycerol, 5% of 2-mercaptoethanol, 0.1% of SDS, 0.025% of bromophenol blue, 62.5 mM Tris pH 6.8), with addition of glass powder, and centrifuged for 10 minutes in an Eppendorf centrifuge at 4° C. 50 µl of the supernatant are applied to native polyacrylamide gel (145× 110×1.2 mm; separating gel: 10% of acrylamide, 0.33% of bisacrylamide, 0.375 M Tris pH 8.8, collecting gel: 5% of acrylamide, 0.165% of bisacrylamide, 0.125 M Tris pH 6.8) and subjected to electrophoresis overnight at 4° C. and 60 V. As soon as the bromophenol blue marker runs out of the gel, the gel is washed twice with distilled water for 10 minutes and once for 30 minutes with reaction buffer (67 mM Tris-maleate, pH 7.1, 42 mM MgCl$_2$, 400 mM ammonium chloride). The gel is placed on a glass plate of the same size and covered with a layer of 40 ml of 1% strength agarose in reaction buffer which contains the substrates kanamycin sulphate (20 µg/ml) and 20–200 µCi of $^{32}$P ATP (Amersham). The sandwich gel is incubated for 30 minutes at room temperature and a sheet of phosphocellulose paper P81 (Whatman) is then laid over the agarose. Four layers of 3 MM filter paper, (Whatman) and a few paper handkerchiefs are stacked on top. The transfer of radioactive kanamycin phosphate phosphorylated in situ onto the P81 paper is stopped after 3–4 hours. The P81 paper is incubated for 30 minutes in a solution of proteinase K and 1% of sodium dodecyl sulphate (SDS) at 60° C. and then washed 3–4 times in 250 ml of 10 mM phosphate buffer pH 7.5 at 80° C., dried and autoradiographed for 1–12 hours at −70° C. (XAR5 film from Kodak).

3. Transformation of Solanum tuberosum (potato)

The transformation was carried out in exactly the manner described in EP-A-0,242,246, pages 14 to 15, the Agrobacteria containing Ti plasmids which carry the CCoAMT gene or the CCoAMT genes.

All the percentage data in the above examples relate to percentages by weight, unless stated otherwise.

The presence of the CCoAMT genes in the plant cells and plants (tobacco) obtained according to the above examples was confirmed by Southern blot analysis, The expression of the CCoAMT genes was detected by Northern blot analysis, and CCoAMT was detected with the aid of specific antibodies.

Some of the media employed in the transformation of plants and plant cells are described below:

| Am medium |
| --- |
| 3.5 g of K$_2$HPO$_4$ |
| 1.5 g of KH$_2$PO$_4$ |
| 0.5 g of Na$_3$ citrate |
| 0.1 g of MgSO$_{45}$ × 7H$_2$O |
| 1 g of (NH$_4$)$_2$SO$_4$ |
| 2 g of glucose to 1 l |

Medium for sterile shoot culture of tobacco
Macroelements ½ of the concentration of the MS salts
Microelements ½ of the concentration of the MS salts
Fe-EDTA Murashige and Skoog (MS)

| | |
| --- | --- |
| Myo-inositol | 100 mg/l |
| Sucrose | 10 mg/l |
| Agar | 8 g/l |
| Vitamins | |
| Ca panthotenate | 1 mg/l |
| Biotin | 10 mg/l |
| Nicotinic acid | 1 mg/l |
| Pyridoxine | 1 mg/l |
| Thiamine | 1 mg/l | pH 5.7 before autoclaving

For culture of *Nicotiana tabacum* petit Havana SR1, *Nicotiana tabacum* Wisconsin 38 and *Nicotiana plumaginifolia* protoplasts (Nagy and Maliga, 1976)

| | | |
| --- | --- | --- |
| Macroelements | NH$_4$NO$_3$ | 250 mg/l |
| | KNO$_3$ | 2500 mg/l |
| | CaCl$_2$.2H$_2$O | 900 mg/l |
| | MgSO$_4$.7H$_2$O | 250 mg/l |
| | NaH$_2$PO$_4$.1H$_2$O | 150 mg/l |
| | (NH$_4$)$_2$SO$_4$ | 134 mg/l |
| | CaHPO$_4$.1H$_2$O | 50 mg/l |
| Microelements | H$_3$BO$_3$ | 3 mg/l |
| | MnSO$_4$.1H$_2$O | 10 mg/l |
| | ZnSO$_4$.4H$_2$O | 2 mg/l |
| | KI | 0.75 mg/l |
| | Na$_2$MoO$_4$.2H$_2$O | 0.25 mg/l |
| | CuSO$_4$.5H$_2$O | 0.025 mg/l |
| | CoCl$_2$.6H$_2$O | 0.025 mg/l |
| Fe-EDTA | Na$_2$EDTA | 37.2 mg/l |
| | Fe$_2$SO$_4$.7H$_2$O | 27.8 mg/l |
| Inositol | | 100 mg/l |
| Sucrose | | 137 g/l |
| | | (= 0.4 M) |
| Xylose | | 250 mg/l |
| Vitamins | Nicotinic acid | 1 mg/l |
| | Pyridoxine | 1 mg/l |
| | Thiamine | 10 mg/l |
| Hormones | NAA | 1.0 mg/l |
| | Kinetin | 0.2 mg/l | pH 5.6
Sterilise filter

Linsmaier and Skoog medium (Linsmaier and Skoog 1965)
For culture of regenerating protoplasts and for tissue culture of tobacco tumours and callus. Linsmaier and Skoog (LS) medium is Murashige and Skoog medium (Murashige and Skoog, 1962) with the following modifications:

thiamine is weighed in at a higher concentration of 0.4 mg/l instead of 0.1 mg/l;
glycine, pyridoxine and nicotinic acid are absent. Macroelements NH$_4$NO$_3$ 1650 mg/l

| | | |
| --- | --- | --- |
| Macroelements | NH$_4$NO$_3$ | 1650 mg/l |
| | KNO$_3$ | 1900 mg/l |
| | CaCl$_2$.2H$_2$O | 440 mg/l |
| | MgSO$_4$.7H$_2$O | 370 mg/l |
| | KH$_2$PO$_4$ | 170 mg/l |
| Microelements | H$_3$BO$_3$ | 6.2 mg/l |
| | MnSO$_4$.1H$_2$O | 22.3 mg/l |
| | ZnSO$_4$.4H$_2$O | 8.6 mg/l |
| | KI | 0.83 mg/l |
| | Na$_2$MoO$_4$.2H$_2$O | 0.25 mg/l |
| | CuSO$_4$.5H$_2$O | 0.025 mg/l |
| | CoCl$_2$.6H$_2$O | 0.025 mg/l |
| Fe-EDTA | Na$_2$EDTA | 37.2 mg/l |
| | Fe$_2$SO$_4$.7H$_2$O | 27.8 mg/l |
| Inositol | | 100 mg/l |
| Sucrose | | 30 g/l |
| Agar | | 8 g/l |
| Vitamins | Thiamine | 0.4 mg/l |
| Hormones: | NAA | 1 mg/l |
| | Kinetin | 0.2 mg/l | pH 5.6 before autoclaving

The following literature can be cited for transformation of plants and plant cells:

Fraley R. T., Rogers S. G., Horsch R. B., Sanders P. R., Flick J. S., Adams S. P., Bittner M. L., Brand L. A., Fink C. L., Fry J. S., Fallupi G. R., Goldberg S. B., Hoffmann N. L., Woo S. C. (1983). Expression of bacterial genes in plant cells. Proc. Natl. Acad. Sci. USA 80:4803–4807.

Fromm M E, Taylor L P, Walbot V (1986) Stable transformation of maize after gene transfer by electroporation. Nature 319: 791–793

Hain, R., Stabel, P., Czernilofsky, A. P., Steinbiβ, H. H., Herrera-Estrella, L., Schell, J. (1985) Uptake, integration, expression and genetic transmission of a selectable chimeric gene by plant protoplasts. Molec Gen Genet 199: 161–168

Hernalsteens J P, Thia-Tong L, Schell J, Van Montagu M 984) An Agrobacterium-transformed Cell culture from the monocot *Asparagus officinalis*. EMBO J 3:3039–3041

Herrera-Estrella L., De Block M., Messens E., Hernalsteens J P., van Montagu M., Schell J. (1983) EMBO J. 2: 987–995.

Horsch R B, Fry J E, Hoffmann N L, Eichholtz D, Rogers S G, Fraley R T (1985) A simple and general method for transferring genes into plants. Science 277: 1229–1231

Krens F H, Molendijk L, Wullems G J, Schilperoort R A (1982) in vitro transformation of plant protoplasts with Ti-plasmid DNA. Nature 296: 72–74

Koncz C, Schell J (1986) The promotor of T$_L$-DNA gene 5 controls the tissue-specific expression of chimaeric genes carried by a noval type of Agrobacterium linary vector. Mol. Gen. Genet. (1986) 204: 338–396 Linsmaier D M, Skoog F (1965) Organic growth factor requirements of tobacco tissue cultures. Physiol plant 18: 100–127

Marton L, Wullems G J, Molendijk L, Schilperoort P R (1979) In vitro transformation of cultured cells from *Nicotiana tabacum* by *Agrobacterium tumefaciens*. Nature 277: 1229–131

Nagy J I, Maliga P (1976) Callus induction and plant regeneration from mesophyll protoplasts of *Nicotiana sylvestris*. Z Pflanzenphysiol 78: 453–455

Paszkowski J, Shillito R D, Saul M, Mandak V, Hohn T, Hohn B, Potrykus I (1984) Direct gene transfer to plants. EMBO J 3: 2717–2722

Shillito R D, Paszkowski J. Potrykus I (1983) Agarose plating and Bead type culture technique enable and stimulate development of protoplast-derived colonies in an number of plant species. Pl Cell Rep 2: 244–247 Van den Elzen P J M, Townsend J, Lee K Y, Bedbrook J R (1985) A chimaeric resistance gen as a selectable marker in plant cells. Plant Mol. Biol. 5, 299–302.

Van den Elzen P J M, Townsend J, Lee K Y, Bedbrook J R (1985) A chimaeric resistance gen as a selectable marker in plant cells. Plant Mol. Biol. 5, 299–302.

Velten J, Velten L, Hain R, Schell J (1984) Isolation of a dual plant promotor fragment from the Ti Plasmid of Agrobacterium tumefaciens. EMBO J 12: 2723–2730

Van Haute E, Joos H, Maes M, Warren G, Van Montagu M, Schell J (1983) Intergenic transfer and excharge recombination of restriction fragments clones in pBR322: a novel strategy for the reversed genetics of Ti plasmids of /Agrobacterium tumefacines. EMBO J 2: 411–418.

Zambryski P, Joos H, Genetello C, van Montagu M, Schell J (1983) Ti-plasmid vector for the introduction of DNA into plant cells without altering their normal regeneration capacity, EMBO J 12: 2143–2150.

Reiss, B., Sprengel, Will H., and Schaller H (1984) A new sensitive method for qualitative and quantitative assay of neomycin phosphotransferase in crude cell tracts, GENE 1081: 211–217

Schreier P. H., Seftor E. A., Schell J. and Bohnert H. J. (1985) The use of nuclear-encoded sequences to direct the light-regulated synthesis and transport of a foreingn protein into plant chloroplasts, EMBO J Vol. 4, No. 1: 25–32

The following published patent applications may furthermore be mentioned:

| | |
|---|---|
| EP-A 116,718 | EP-A-126,546 |
| EP-A 159,418 | EP-A-164,597 |
| EP-A 120,515 | EP-A-175,966 |
| EP-A-120,516 | WO 84/02913 |
| EP-A-172,112 | WO 84/02919 |
| EP-A-140,556 | WO 84/02920 |
| EP-A-174,166 | WO 83/01176 |
| EP-A-122,791 | |

The increased resistance of the transformed plants according to the invention may be illustrated with the aid of the following example:

Detection of the increased resistance of transformed plants

EXAMPLE A

To test for an increased resistance to plant diseases, the plants are inoculated with a pathogen and the degree of attack is used as parameter. Botrytis cinerea Pers. is used as the test pathogen.

The tobacco plants are pregrown in tissue culture and subsequently potted in standard soil (Balster) in pots (d=11 cm) in a greenhouse and grown in the greenhouse at 23° C. and 70–80% relative atmospheric humidity until the start of the experiment. The plants are supplied with water and fertiliser as required. For inoculation, the leaves of the plants (3–4 weeks after transfer into the greenhouse) are sprayed with a spore suspension of the pathogen until dripping wet. The plants are then incubated at 100% relative atmospheric humidity and 10–20° C. After 4–8 days, the state of health of the plants is determined in per cent with the aid of the leaf area attacked.

The transformed tobacco plants into which a CCoAMT gene according to the invention had been inserted exhibit a significantly lower attack by B. cinerea than the of the non-transformed plants.

| Abbreviations used: | |
|---|---|
| 1 | Start of the encoding region |
| 2 | End of the encoding region |
| CaMV | Cauliflower mosaic virus |
| $Cb^R$ | Carbenicillin resistance gene |
| E | EcoRI Cleavage site |
| H | HindIII cleavage site |
| $Km^R$ | Kanamycin resistance gene for plants |
| P35S | CaMV35S promotor |
| pA35S | Polyadenylation sequence of CaMV |
| RV | EcoRV |
| S | SST1 cleavage site |
| Arrow direction | Direction of the promotor and of the gene |
| LB | Left border sequence of the T-DNA of A. tumefaciens |
| RB | Right border sequence of the T-DNA of A. tumefaciens |

Preferred hybridisation conditions

As mentioned above, the preferred CCoAMT genes according to the invention are characterised in that they hybridise with the CCoAMT-cDNA sequence contained in the plasmid pL2-4 or its components or with the cDNA sequence according to SEQ ID No: 1 or its components and encode CCoAMT.

Preferably moderate stringency conditions are used. Moderate stringency conditions means preferably at 58 to 65° C. (particularly preferred at 63° C.) in 3 to 4 times concentrated SSC.

If this method is used to isolate CCoAMT genes from other sources, normally a population of cDNA's with related sequences are obtained which can e. g. be expressed in E. coli. The enzyme activity can be determined (e. g. according to Pakusch et al, Arch. Biochem. Biophys. 271 (1989), pp. 488–494) and the desired cDNA can be isolated.

What is claimed is:

1. A transgenic plant cell, said plant cell comprising DNA inserted into its genome, said plant cell expressing said DNA, and said DNA comprising a nucleotide sequence that encodes the caffeoyl-CoA 3-O-methyltransferase encoded by the nucleotide sequence of SEQ ID NO; 1.

2. A transgenic whole plant, said whole plant comprising DNA inserted into its genome, said whole plant expressing said DNA, nd said DNA comprising a nucleotide sequence that encodes the caffeoyl-CoA 3-O-methyltransferase encoded by the nucleotide sequence of SEQ ID NO; 1.

3. A transgenic plant part, said plant part comprising DNA inserted into its genome, said plant part expressing said DNA, and said DNA comprising a nucleotide sequence that encodes the caffeoyl-CoA 3-O-methyltransferase encoded by the nucleotide sequence of SEQ ID NO: 1.

4. A transgenic plant seed, said plant seed comprising DNA inserted into its genome, said plant seed expressing said DNA, and said DNA comprising a nucleotide sequence that encodes the caffeoyl-CoA 3-O-methyltransferase encoded by the nucleotide sequence of SEQ ID NO: 1.

* * * * *

UNITED STATES PATENT AND TRADEMARK OFFICE
CERTIFICATE OF CORRECTION

PATENT NO. : 6,160,205  
DATED : December 12, 2000  
INVENTOR(S) : Matern et al.

Page 1 of 1

It is certified that error appears in the above-identified patent and that said Letters Patent is hereby corrected as shown below:

Column 19,  
Line 51, delete "nd" and substitute -- and --

Signed and Sealed this

Fourteenth Day of May, 2002

Attest:

JAMES E. ROGAN  
Attesting Officer *Director of the United States Patent and Trademark Office*